US009469598B2

(12) United States Patent
Tanaka et al.

(10) Patent No.: US 9,469,598 B2
(45) Date of Patent: Oct. 18, 2016

(54) ERYTHROPOIETIN PRODUCTION-PROMOTING AGENT

(71) Applicants: SBI Pharmaceuticals Co., Ltd., Tokyo (JP); Tohuku University, Miyagi (JP)

(72) Inventors: Tohru Tanaka, Tokyo (JP); Motowo Nakajima, Tokyo (JP); Kiwamu Takahashi, Tokyo (JP); Takaaki Abe, Miyagi (JP)

(73) Assignees: SBI Pharmaceuticals Co., Ltd., Tokyo (JP); Tohoku University, Miyagi (JP)

( * ) Notice: Subject to any disclaimer, the term of this patent is extended or adjusted under 35 U.S.C. 154(b) by 16 days.

(21) Appl. No.: 14/350,522

(22) PCT Filed: Oct. 5, 2012

(86) PCT No.: PCT/JP2012/075947
§ 371 (c)(1),
(2) Date: Apr. 8, 2014

(87) PCT Pub. No.: WO2013/054755
PCT Pub. Date: Apr. 18, 2013

(65) Prior Publication Data
US 2014/0288172 A1    Sep. 25, 2014

(30) Foreign Application Priority Data

Oct. 12, 2011  (JP) ................. 2011-225382
Oct. 12, 2011  (JP) ................. 2011-225383
Mar. 30, 2012  (JP) ................. 2012-081581

(51) Int. Cl.
| | | |
|---|---|---|
| *A61K 31/295* | (2006.01) | |
| *A01N 55/02* | (2006.01) | |
| *C07C 217/08* | (2006.01) | |
| *A61K 31/197* | (2006.01) | |
| *A61K 31/28* | (2006.01) | |
| *A61K 33/06* | (2006.01) | |
| *A61K 33/26* | (2006.01) | |
| *A61K 33/30* | (2006.01) | |
| *A61K 45/06* | (2006.01) | |
| *A61K 31/221* | (2006.01) | |
| *A61K 31/195* | (2006.01) | |

(52) U.S. Cl.
CPC .......... *C07C 217/08* (2013.01); *A61K 31/195* (2013.01); *A61K 31/197* (2013.01); *A61K 31/221* (2013.01); *A61K 31/28* (2013.01); *A61K 31/295* (2013.01); *A61K 33/06* (2013.01); *A61K 33/26* (2013.01); *A61K 33/30* (2013.01); *A61K 45/06* (2013.01)

(58) Field of Classification Search
CPC ............ A61K 31/195; A61K 31/197; A61K 31/221; A61K 31/28; A61K 31/295; A61K 33/06; A61K 33/26; A61K 33/30; A61K 45/06; C07C 217/08
USPC .......................... 514/502; 560/170; 562/567
See application file for complete search history.

(56) References Cited

U.S. PATENT DOCUMENTS

| | | | |
|---|---|---|---|
| 9,018,257 B2 * | 4/2015 | Rephaeli | A61K 31/197 514/547 |
| 9,095,165 B2 * | 8/2015 | Tanaka | A23L 1/30 |
| 2004/0234555 A1 | 11/2004 | Oshida et al. | |
| 2005/0020487 A1 * | 1/2005 | Klaus | A61K 31/00 514/183 |
| 2008/0026075 A1 | 1/2008 | Kondo et al. | |
| 2008/0214653 A1 | 9/2008 | Zicker et al. | |
| 2008/0287368 A1 | 11/2008 | Yu et al. | |
| 2014/0256806 A1 * | 9/2014 | Tanaka | A61K 31/197 514/502 |
| 2015/0290159 A1 * | 10/2015 | Tanaka | A23L 1/30 514/502 |

FOREIGN PATENT DOCUMENTS

| | | |
|---|---|---|
| CN | 1538839 A | 10/2004 |
| CN | 102164596 A | 8/2011 |
| EP | 1413303 A1 | 4/2004 |
| JP | 2003-040770 A | 2/2003 |
| JP | 2006-008720 A | 1/2006 |
| JP | 2006-069963 A | 3/2006 |
| JP | 2008-536935 A | 9/2008 |
| JP | 2009-504766 A | 2/2009 |
| JP | 2009/298739 A | 12/2009 |
| JP | 2011-016753 A | 1/2011 |
| JP | 5295652 B2 | 9/2013 |
| WO | 2004/091495 A2 | 10/2004 |

OTHER PUBLICATIONS

Berkovitch-Luria et al., "A multifunctional 5-aminolevulinic acid derivative induces erythroid differentiation of K562 human erythroleukemic cells", Available online Jun. 13, 2012, European Journal of Pharmaceutical Sciences, 47(1), pp. 1-294.*
EPO Communication with Extended European Search Report dated Apr. 10, 2015, issued by the European Patent Office in corresponding European Patent Application No. EP-12839684.3 (8 pages).

(Continued)

*Primary Examiner* — My-Chau T Tran
(74) *Attorney, Agent, or Firm* — Osha Liang LLP

(57) ABSTRACT

A therapeutic and/or prophylactic agent for renal anemia comprising ALAs and an erythropoietin production promoter comprising ALAs.

14 Claims, 1 Drawing Sheet

(56) References Cited

OTHER PUBLICATIONS

Ishizuka, M., et al., "Agent for reducing optical damage e.g. photodermatosis caused during administration of 5-aminolevulinic acid or its salt or derivative(s), comprises iron compound as active ingredient"; WPI/Thomson, vol. 2010, No. 3, Dec. 24, 2009 (Dec. 24, 2009); XP002736347. (4 pages) [See Also: Corresponding JP-2009298739 and JP-5295652.

Ienaga, Kazuharu, et al., "First Indications Demonstrating the Preventive Effects of NZ-419, a Novel Intrinsic Antioxidant, on the Initiation and/or Progression of Chronic Renal Failure in Rats"; Biol. Pharma. Bull., vol. 32, No. 7, 2009; pp. 1204-1208.

Neumcke, Imke, et al., "Effects of Pro- and Antioxidative Compounds on Renal Production of Erythropoietin"; Endocrinology, vol. 140, No. 2, 1999; pp. 641-645.

Jensen, J.D., et al., "Reducted Production, absorption, and Elimination of Erythropoietin in Uremia Compared With Healthy Volunteers"; Journal of the American Society of Nephrology, vol. 5, No. 2, 1994; pp. 177-185.

"2008 JSDT Guideline for Renal Anemia in Chronic Kidney Disease—4. Treatment for Renal Anemia"; 41(10); pp. 661-716, with partial English translation of p. 674. (21 pages).

International Search Report mailed Dec. 11, 2012, in corresponding International Application No. PCT/JP2012/075947, with English translation (6 pages).

First Office Action and Search Report issued by the State Intellectual Property Office of the People's Republic of China on Jul. 1, 2015, in corresponding Chinese Patent Application No. 201280060344.0 (9 pages), with English translation (11 pages).

Second Office Action issued in Chinese Application No. 201280060344.0; Dated Jan. 25, 2016 (19 pages).

Ma Jianfei, et al., "Discussion of Mechanism of Erythropoietin Treating Renal Anemia", Chinese Journal of Nephrology, vol. 13, No. 6, 19971231, 372-373 (2 pages).

Office Action issued in corresponding Taiwanese Application No. 101137457 dated Jan. 21, 2016 (6 pages).

Tehuang Tseng et al., "The Synthesis of Daidzein Derivatives," Journal directory listing, vol. 30 (1985), pp. 537-545.

\* cited by examiner

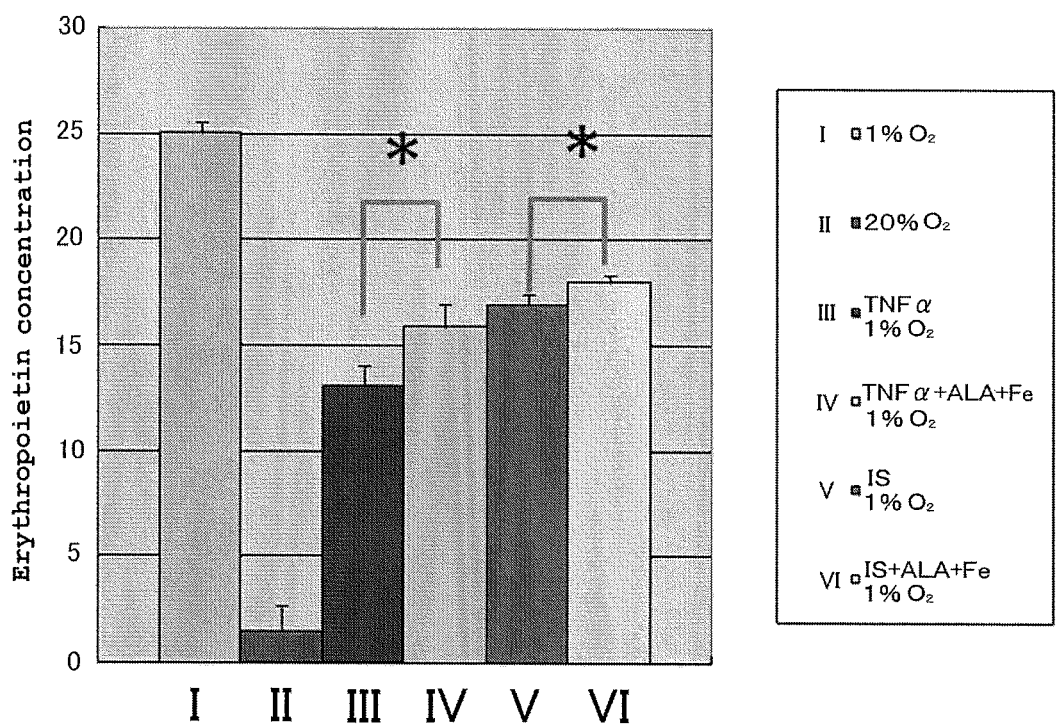

ERYTHROPOIETIN PRODUCTION-PROMOTING AGENT

CROSS REFERENCE TO RELATED APPLICATIONS

This is a national stage application based on PCT/JP2012/075947, filed on Oct. 5, 2012, which claims priority to Japanese Patent Application Nos. 2011-225382, filed on Oct. 12, 2011, 2011-225383, filed on Oct. 12, 2011, and 2012-081581, filed on Mar. 30, 2012. This application claims the priority of these prior applications and incorporates their disclosures by reference in their entireties.

TECHNICAL FIELD

The present invention relates to an erythropoietin production promoter. More specifically, the present invention relates to an erythropoietin production promoter comprising ALAs.

The present invention also relates to a therapeutic and/or prophylactic agent for anemia arising from the reduction of erythropoietin production ability, typically renal anemia. More specifically, the present invention relates to a therapeutic and/or prophylactic agent for anemia comprising ALAs.

BACKGROUND ART

Kidney is the main organ that produces erythropoietin, and erythropoietin is mainly produced in tubulointerstitial cells in the kidney.

Erythropoietin is a hormone consisting of 165 amino acids. Erythropoietin binds to a receptor on an erythroid progenitor cell in the hematopoietic tissue, and promotes the proliferation and differentiation of the erythroid progenitor cell. In this way, erythropoietin modulates the production of erythrocytes.

Under normal circumstances, the production of erythropoietin is regulated by oxygen partial pressure in the blood, thereby regulating the production of erythrocytes. When anemic, the kidney increases the production of erythropoietin in order to orient towards hematopoiesis, and as a result erythropoietin in the blood increases.

However, when the production of erythropoietin in the kidney is reduced due to kidney disorder etc., erythropoietin in the blood will not be increased even when anemic, and a pathological state is triggered where the production of erythrocytes is suppressed. Such a pathological state is renal anemia. In other words, renal anemia is an anemia arising mainly from the reduction of erythropoietin (EPO) production in the kidney due to kidney disorder etc. Among renal diseases, particularly in the case of a chronic renal disease, renal anemia does not necessarily occur because the decrease in renal function progresses gradually. However, in the case of an acute renal disease such as renal failure among renal diseases, it is known that renal anemia occurs at a high probability. In addition, numerous cases of anemia are seen which are caused by the reduction of erythropoietin production totally unrelated to the onset of renal disease. Thus, anemia arising from the reduction of erythropoietin including renal disease, in particular chronic renal disease does not have the same onset mechanism as renal anemia.

Examples of characteristic symptoms of renal anemia include shortness of breath, palpitation, dizziness, decreased appetite, and lassitude.

It is known that uremia also occurs in a patient with progressed renal failure. Uremia is a pathological state where waste products such as urea remain in the blood due to decrease in renal function. Uremic patients develop various symptoms, and the symptom of renal anemia is one of them.

ESA (erythrocyte hematopoietic stimulating factor preparation) has been developed and been put to practical application as a method for treating such renal anemia. Examples of ESA include (1) erythropoietin, (2) erythropoietin derivative, and (3) other compounds that stimulate erythropoietin receptor.

The therapeutic policy for renal anemia in Japan is implemented based on the following guidelines (Non-Patent Document 1).

1) ESA (erythrocyte hematopoietic stimulating factor preparation) therapy should be initiated when diagnosis of renal anemia is confirmed and administration criteria are satisfied (active recommendation).

2) Administration of iron preparation necessary for hematopoiesis should be used in combination (active recommendation).

3) Make effort to clean the dialysate and perform sufficient dialysis in maintenance hemodialysis (HD) patients (active recommendation).

4) In patients with nutrient disorder or inflammation, active therapy against these should be performed (active recommendation).

As shown in the above guidelines, ESA is recommended as the first-line drug for renal anemia therapeutic agent in Japan.

However, it is known that some renal anemia patients show resistance to ESA therapy. There are still many unclear points regarding the mechanism of why the reactivity produced towards ESA therapy is low. As one of the reasons for such low reactivity towards ESA therapy, increase in blood concentration of inflammatory cytokines such as TNF-α and IL-6 is thought to be an active reason. Inflammatory cytokine is a causative factor that causes various inflammation symptoms in vivo. Inflammatory cytokine is also known to shorten the lifespan of erythrocytes. Inflammatory cytokine is also known to reduce the production of erythropoietin by erythropoietin producer cells. Accordingly, inflammatory cytokine is thought to be a causative substance that causes anemia.

ESA therapy also has the risk of causing thrombosis or myocardial infarction etc. as its side effect. Poor prognosis of malignant tumors has also been reported recently.

As stated above, ESA therapy is merely a palliative therapy, and does not possess an action to restore the reduction of erythropoietin production by erythropoietin producer cells.

There was further a problem regarding compliance since oral administration of ESA is typically difficult.

CITATION LIST

Non-Patent Literature

Non-Patent Document 1
 Guideline for Renal Anemia in Chronic Kidney Disease

SUMMARY OF THE INVENTION

Problems to be Solved by the Invention

The present invention provides an erythropoietin production promoter for a cell, and a method for treating and/or preventing anemia, in particular renal anemia is provided by a new approach that is different from a palliative therapy agent such as ESA (erythrocyte hematopoietic stimulating factor preparation).

Means for Solving the Problems

As a result of extensive investigations, the present inventors have surprisingly found that ALAs suppress the reduction of erythropoietin production by erythropoietin producer cells.

This shows that ALAs are effective for basic remedy and prevention of anemia arising from the reduction of erythropoietin production.

As stated above, renal anemia is a typical anemia arising from the reduction of erythropoietin production, in other words, a pathological state caused by the reduction of erythropoietin production by erythropoietin producer cells in the kidney. Accordingly, the following description will be in regards to "renal anemia" as the representative anemia arising from the reduction of erythropoietin production, but anemia to be the subject of the present invention is not limited to renal anemia.

The present invention allows therapy against a more primary cause of renal anemia.

More specifically, as a result of extensive investigations, the present inventors have surprisingly found that ALAs suppress the reduction of erythropoietin production by erythropoietin producer cells caused by inflammatory cytokine or uremic toxin.

In regards to the relationship between anemia and ALA, it is known that ALA is effective in preventing piglet anemia (see Japanese Patent No. 4754731). Piglet anemia occurs because hematopoiesis cannot catch up to rapid growth, and it is reported that supplement of ALA as one of the compounds necessary for hematopoiesis is effective. The action mechanism of this is that ALA is a substance that exists in vivo, and ALA is converted into heme to augment hemoglobin. However, this has no relationship whatsoever with the mechanism of the present invention where ALAs suppress the reduction of erythropoietin production by erythropoietin producer cells.

The present inventors have also gained the following knowledge as disclosed in already filed but still unpublished applications. Several of these are base applications for claiming priority to the present application.

In other words, the present inventors have found that ALAs have an effect of improving cancerous anemia. However, this is thought to be the suppression of cancer-specific hemolytic reaction. The present inventors have also found that ALAs have the effect of improving/preventing chronic renal disease. However, this directly improves the filtration ability of the kidney, and has no relationship whatsoever with the mechanism of the present invention where the reduction of erythropoietin production is suppressed by erythropoietin producer cells. The present inventors have also found that ALAs have a therapeutic/prophylactic effect for sepsis. However, this is based on the effect of suppressing the production of inflammatory cytokine per se, and has no relationship whatsoever with the mechanism of the present invention where the reduction of erythropoietin production is suppressed by erythropoietin producer cells.

Accordingly, the characteristic of the present invention that the reduction of erythropoietin production is suppressed by erythropoietin producer cells cannot be envisioned from conventional prior art or the unpublished applications by the present inventors which are prior applications. Elucidation of the exact mechanism of why ALAs are effective in improving erythropoietin production ability is a future task.

In other words, the present invention relates to an erythropoietin production promoter comprising a compound shown by the following Formula (I):

$$R^1\text{—NHCH}_2\text{COCH}_2\text{CH}_2\text{COOR}^2 \qquad (I)$$

(wherein $R^1$ represents a hydrogen atom or an acyl group, and $R^2$ represents a hydrogen atom, a linear or branched alkyl group, a cycloalkyl group, an aryl group, or an aralkyl group.) or a salt thereof.

The present invention also relates to a method of promoting the production of erythropoietin, characterized in administering to a subject a therapeutically effective amount of a compound shown by the following Formula (I):

$$R^1\text{—NHCH}_2\text{COCH}_2\text{CH}_2\text{COOR}^2 \qquad (I)$$

(wherein $R^1$ represents a hydrogen atom or an acyl group, and $R^2$ represents a hydrogen atom, a linear or branched alkyl group, a cycloalkyl group, an aryl group, or an aralkyl group.)
or a salt thereof.

The present invention also relates to a therapeutic and/or prophylactic agent for anemia arising from the reduction of erythropoietin production comprising a compound shown by the following Formula (I):

$$R^1\text{—NHCH}_2\text{COCH}_2\text{CH}_2\text{COOR}^2 \qquad (I)$$

(wherein $R^1$ represents a hydrogen atom or an acyl group, and $R^2$ represents a hydrogen atom, a linear or branched alkyl group, a cycloalkyl group, an aryl group, or an aralkyl group.)
or a salt thereof.

The reduction of erythropoietin production may be those caused by inflammatory cytokine or uremic toxin.

In each of the above Formula (I),
$R^1$ can be selected from the group consisting of a hydrogen atom, an alkanoyl group having 1 to 8 carbons, and an aroyl group having 7 to 14 carbons, and
$R^2$ can be selected from the group consisting of a hydrogen atom, a linear or branched alkyl group having 1 to 8 carbons, a cycloalkyl group having 3 to 8 carbons, an aryl group having 6 to 14 carbons, and an aralkyl group having 7 to 15 carbons.

The therapeutic and/or prophylactic agent of the present invention for anemia arising from the reduction of erythropoietin production can further contain one or two or more metal-containing compounds. Said metal-containing compound may be a compound containing a metal selected from the group consisting of iron, magnesium, and zinc.

In the therapeutic and/or prophylactic agent of the present invention for anemia arising from the reduction of erythropoietin production, the said anemia may be renal anemia.

Effects of the Invention

The production of erythropoietin by erythropoietin producer cells can be promoted by the use of the erythropoietin production promoter of the present invention. As a result, this will be effective for basic remedy and prevention of anemia arising from the reduction of erythropoietin production, typically renal anemia.

In other words, the present invention provides a therapeutic and/or prophylactic agent for renal anemia.

Therapy in the present invention comprises not only completely curing renal anemia, but also improving the symptoms of renal anemia. Similarly, prevention comprises not only completely stopping the symptoms of renal anemia from occurring, but also allowing the symptoms of renal anemia which will have occurred without administering the prophylactic agent of the present invention to be milder.

By using the erythropoietin production promoter of the present invention, the reduction of erythropoietin production by erythropoietin producer cells can be suppressed, and anemia, in particular renal anemia can be treated and/or prevented.

Accordingly, the present invention provides a method for treating and/or preventing renal anemia by a new approach that is different from a palliative therapy agent such as ESA (erythrocyte hematopoietic stimulating factor preparation).

The therapeutic and/or prophylactic agent of the present invention for renal anemia can further be used instead of or in combination with ESA therapy, thereby decreasing the side effects due to using ESA therapy alone.

The present invention also provides an erythropoietin production promoter.

The production of erythropoietin by erythropoietin producer cells can be promoted by using the erythropoietin production promoter of the present invention.

BRIEF DESCRIPTION OF THE DRAWINGS

FIG. 1 is a graph showing the result of measuring the erythropoietin concentration contained in the culture supernatant after culturing liver cancer cells producing erythropoietin (HEP3B cell) under 6 different conditions for 24 hours.

DESCRIPTION OF EMBODIMENTS

Renal anemia in the present invention is an anemia mainly arising from the reduction of erythropoietin production in the kidney due to kidney disorder etc. The reduction of erythropoietin production in the kidney herein includes those caused by inflammatory cytokine or uremic toxin. Uremic toxin herein includes e.g. indoxyl sulfate.

The therapeutic and/or prophylactic agent of the present invention for renal anemia is not particularly limited as long as it is a therapeutic and/or prophylactic agent for renal anemia comprising ALAs.

In addition, the erythropoietin production promoter of the present invention is not particularly limited as long as it is an erythropoietin production promoter comprising ALAs.

ALAs herein refer to ALA or a derivative thereof or a salt thereof.

ALA herein means 5-aminolevulinic acid. ALA, also referred to as δ-aminolevulinic acid, is a type of amino acid.

Examples of ALA derivatives can include compounds represented by the following Formula (I). In Formula (I), $R^1$ represents a hydrogen atom or an acyl group, and $R^2$ represents a hydrogen atom, a linear or branched alkyl group, a cycloalkyl group, an aryl group, or an aralkyl group. In Formula (I), ALA corresponds to the case where $R^1$ and $R^2$ are hydrogen atoms.

$$R^1\text{—NHCH}_2\text{COCH}_2\text{CH}_2\text{COOR}^2 \qquad (I)$$

ALAs may be those that act in vivo as an active ingredient as the ALA of Formula (I) or a derivative state thereof, and can also be administered as a prodrug (precursor) that is degraded by an in vivo enzyme.

The acyl group in $R^1$ of Formula (I) can include a linear or branched alkanoyl group having 1 to 8 carbons such as formyl, acetyl, propionyl, butyryl, isobutyryl, valeryl, isovaleryl, pivaloyl, hexanoyl, octanoyl, and benzylcarbonyl groups, and an aroyl group having 7 to 14 carbons such as benzoyl, 1-naphthoyl, and 2-naphthoyl groups.

The alkyl group in $R^2$ of Formula (I) can include a linear or branched alkyl group having 1 to 8 carbons such as methyl, ethyl, propyl, isopropyl, butyl, isobutyl, sec-butyl, tert-butyl, pentyl, isopentyl, neopentyl, hexyl, heptyl, and octyl groups.

The cycloalkyl group in $R^2$ of Formula (I) can include a cycloalkyl group having 3 to 8 carbons with saturated or possibly partially unsaturated bonds, such as cyclopropyl, cyclobutyl, cyclopentyl, cyclohexyl, cycloheptyl, cyclooctyl, cyclododecyl, and 1-cyclohexenyl groups.

The aryl group in $R^2$ of Formula (I) can include an aryl group having 6 to 14 carbons such as phenyl, naphthyl, anthryl, and phenanthryl groups.

The aralkyl group in $R^2$ of Formula (I) can include the same exemplification as the above aryl groups for the aryl moiety and the same exemplification as the above alkyl groups for the alkyl moiety, specifically, an aralkyl group having 7 to 15 carbons such as benzyl, phenethyl, phenylpropyl, phenylbutyl, benzhydryl, trityl, naphthylmethyl, and naphthylethyl groups.

Preferred ALA derivatives include compounds where $R^1$ is e.g. a formyl, an acetyl, a propionyl, or a butyryl group. Preferred ALA derivatives also include compounds where the above $R^2$ is e.g. a methyl, an ethyl, a propyl, a butyl, or a pentyl group. Preferred ALA derivatives also include compounds where the combination of the above $R^1$ and $R^2$ is each a combination of (formyl and methyl), (acetyl and methyl), (propionyl and methyl), (butyryl and methyl), (formyl and ethyl), (acetyl and ethyl), (propionyl and ethyl), or (butyryl and ethyl).

Among ALAs, examples of a salt of ALA or a derivative thereof can include a pharmaceutically acceptable acid addition salt, a metal salt, an ammonium salt, and an organic amine addition salt. Examples of an acid addition salt can be, for example, each of inorganic acid salts such as hydrochloride, hydrobromide, hydroiodide, phosphate, nitrate, and sulfate salts, and each of organic acid addition salts such as formate, acetate, propionate, toluenesulfonate, succinate, oxalate, lactate, tartrate, glycolate, methanesulfonate, butyrate, valerate, citrate, fumarate, maleate, and malate salts. Examples of a metal salt can be each of alkali metal salts such as lithium, sodium, and potassium salts, each of alkaline earth metal salts such as magnesium and calcium salts, and each of metal salts such as aluminum and zinc salts. Examples of an ammonium salt can be alkyl ammonium salts such as ammonium and tetramethylammonium salts. Examples of an organic amine salt can include each of triethylamine, piperidine, morpholine, and toluidine salts. These salts can also be employed as a solution at the time of use.

Among the above ALAs, the most preferred are ALA and various esters such as ALA methyl ester, ALA ethyl ester, ALA propyl ester, ALA butyl ester, and ALA pentyl ester, as well as hydrochloride, phosphate, and sulfate salts thereof. Among these, ALA hydrochloride and ALA phosphate salts can be exemplified as particularly preferable.

The above ALAs can be produced by e.g. a well-known method such as chemical synthesis, microorganic production, and enzymatic production. The above ALAs may also form a hydrate or a solvate, and ALAs can be employed alone or in an appropriate combination of two or more.

The erythropoietin production promoter of the present invention or the therapeutic and/or prophylactic agent of the present invention for renal anemia is preferably those further containing a metal-containing compound in a range that does not cause symptoms due to excess. A metal compound can be favorably employed as said metal-containing compound, as long as it does not adversely affect the advantages of the present invention. The metal moiety of the metal-containing compound according to the present invention can include iron, magnesium, zinc, nickel, vanadium, cobalt, copper, chromium, and molybdenum, although iron, magnesium, and zinc are preferred, and iron is a particularly preferred example.

Examples of an iron compound can include ferrous citrate, sodium ferrous citrate, iron sodium citrate, iron ammonium citrate, ferric pyrophosphate, heme iron, iron dextran, iron lactate, ferrous gluconate, iron sodium diethylenetriaminepentaacetate, iron ammonium diethylenetriamine pentaacetate, iron sodium ethylenediaminetetraacetate, iron ammonium ethylenediaminepentaacetate, triethylenetetramine iron, iron sodium dicarboxymethylglutamate, iron ammonium dicarboxymethylglutamate, lactoferrin iron, transferrin iron, ferric chloride, iron sesquioxide, sodium iron chlorophyllin, ferritin iron, ferrous fumarate, ferrous pyrophosphate, saccharated iron oxide, iron acetate, iron oxalate, ferrous succinate, iron sodium succinate citrate, iron sulfate, and iron glycine sulfate. Among these, ferrous citrate and sodium ferrous citrate are preferred.

Zinc compounds can include zinc chloride, zinc oxide, zinc nitrate, zinc carbonate, zinc sulfate, zinc diammonium diethylenetriaminepentaacetate, zinc disodium ethylenediaminetetraacetate, zinc protoporphyrin, and zinc-containing yeast.

One or two or more of each of the above metal-containing compounds can be employed, and the administration dose of the metal-containing compound can include a molar ratio of 0.01 to 10-folds, preferably 0.1 to 5-folds, and more preferably 0.2 to 2-folds relative to the administration dose of ALAs.

The ALAs and the metal-containing compound contained in the erythropoietin production promoter of the present invention or the therapeutic and/or prophylactic agent of the present invention for renal anemia can be administered as a composition comprising the ALAs and the metal-containing compound or as each alone, but simultaneous administration is preferred even when they are each administered alone. However, it may not need to be strictly simultaneous, but may be performed without a substantial interval between the two so that the administration of the ALAs and the metal-containing compound can show an additive or synergistic effect.

Examples of the administration route for the erythropoietin production promoter of the present invention or the therapeutic and/or prophylactic agent of the present invention for renal anemia can include oral administration including sublingual administration, or parenteral administration such as inhalation administration, intravenous administration including infusion, transdermal administration by e.g. a poultice, suppository, or administration by forced enteral nutrient employing a nasogastric tube, a nasointestinal tube, a gastrostomy tube, or an enterostomy tube, but oral administration is used in general.

The administration subject is typically a human, but a non-human animal such as a pet, an experiment animal, and a farm animal may also be included.

The dosage form of the erythropoietin production promoter of the present invention or the therapeutic and/or prophylactic agent of the present invention for renal anemia can be appropriately determined depending on the above administration routes, and can include, for example, injections, infusions, tablets, capsules, fine granules, powders, solutions, liquors dissolved e.g. in a syrup, poultices, and suppositories.

In order to prepare the erythropoietin production promoter of the present invention or the therapeutic and/or prophylactic agent of the present invention for renal anemia, a pharmaceutically acceptable carrier, excipient, diluent, additive, disintegrant, binder, coating, lubricant, gliding agent, glossing agent, flavoring agent, sweetening agent, solubilizer, solvent, gelling agent, and nutrient etc. can be added as necessary, specific examples of which can be water, saline, animal fat and oil, vegetable oil, lactose, starch, gelatin, crystalline cellulose, gum, talc, magnesium stearate, hydroxypropylcellulose, polyalkylene glycol, polyvinyl alcohol, and glycerin. When the therapeutic and/or prophylactic agent of the present invention for renal anemia or the erythropoietin production promoter of the present invention is prepared as an aqueous solution, care must be taken so that the aqueous solution will not be alkaline in order to prevent the degradation of ALAs. If it becomes alkaline, degradation can also be prevented by removing oxygen.

The amount/frequency/duration of the erythropoietin production promoter of the present invention or the therapeutic and/or prophylactic agent of the present invention for renal anemia will vary according to the age, weight, and symptoms etc. of the renal anemia patient. Examples of the preferred administration dose can include 1 mg to 3000 mg/day, preferably 2 mg to 1000 mg/day, and more preferably 3 mg to 700 mg/day per one adult in terms of ALA/phosphate salt. The preferred administration dose can be calculated by molar conversion when other ALAs are employed. Note that the above preferred administration dose range are exemplary and are not limiting.

Examples of the administration frequency can be an administration at once to multiple times a day or a continuous administration by e.g. infusion. The administration duration can also be determined by a method known to a pharmacologist or a clinician of the related technical field based on an index that allows diagnosis of renal anemia such as blood Hb (hemoglobin) value or erythropoietin concentration.

When the erythropoietin production promoter of the present invention is employed as a therapeutic and/or prophylactic agent for renal anemia, it can also be used in combination with other existing therapeutic and/or prophylactic agents for renal anemia. An Example of existing therapeutic and/or prophylactic agents for renal anemia can include ESA (erythrocyte hematopoietic stimulating factor preparation) used in ESA therapy. Non-limiting examples of such ESA (erythrocyte hematopoietic stimulating factor preparation) can include a recombinant human erythropoietin preparation (rHu erythropoietin) such as Epoetin α™, Epoetin β™, and Darbepoetin α™. Since the mechanisms of these agents and ALA regarding the renal anemia therapeutic and/or prophylactic agent are each thought to be fundamentally different, additive or in some cases synergistic effect can be expected.

Except when expressly defined, the terms used herein are employed to describe a particular embodiment and do not intend to limit the invention.

In addition, the term "comprising" as used herein, unless the content clearly indicates to be understood otherwise, intends the presence of the described items (such as components, steps, elements, and numbers), and does not exclude the presence of other items (such as components, steps, elements, and numbers).

Unless otherwise defined, all terms used herein (including technical and scientific terms.) have the same meaning as that broadly recognized by those skilled in the art of the technology to which the present invention belongs. Unless explicitly defined otherwise, the terms used herein should be construed to have meanings consistent with those herein and in the related technical fields, and are not to be construed as idealized or excessively formal meanings.

The present invention will now be described in further detail referring to Examples. However, the present invention can be embodied by various aspects, and shall not be construed as being limited to the Examples described herein.

EXAMPLES

Example 1

Measurement of Improvement Effect of Erythropoietin Production Ability after Administration of ALAs to Cells with Reduced Erythropoietin Production Ability Erythropoietin production ability of erythropoietin producer cells were reduced by culturing the erythropoietin producer cells under hypoxic condition to allow artificial production of erythropoietin, and then adding inflammatory cytokine or uremia toxin.

TNF-α was employed as the inflammatory cytokine. In addition, indoxyl sulfate was employed as the uremic toxin. Indoxyl sulfate is thought to be the causative substance of uremic toxin, and is also the most commonly used uremia-related marker. Indoxyl sulfate in vivo is also a substance where tryptophan-derived indoles are sulfated and synthesized in the liver. Accordingly, a state of reduced erythropoietin production by addition of inflammatory cytokine or uremic toxin is a state of mimicked renal anemia. The present inventors have found that the reduction of erythropoietin production is suppressed in said state by administration of ALAs.

In this Example, HEP3B cells which are liver cancer cells that produce erythropoietin of Groups I to VI with different culture conditions (from ATCC) were used. First, as a culturing step common to all 6 groups, about 300,000 HEP3B cells per well of a 12-well plate were cultured. The culture condition employed was culturing in RPMI1640 medium supplemented with 10% FCS/PC-SM at 37° C. under 20% oxygen condition. After 24 hours of culture, they were divided into the following culture conditions I to VI, and further cultured for 24 hours. Human recombinant TNF-a (rhTNF-a; Roche) was employed as TNF-α in the following.

TABLE 1

| Group | Condition |
|---|---|
| I) | Under 1% oxygen condition |
| II) | Under 20% oxygen condition |
| III) | Under 1% oxygen condition, 220 U/ml TNF-α |
| IV) | Under 1% oxygen condition, 220 U/ml TNF-α 0.3 μM 5-aminolevulinic acid hydrochloride, 0.15 μM sodium ferrous citrate |
| V) | Under 1% oxygen condition, 1 mM indoxyl sulfate |
| VI) | Under 1% oxygen condition, 1 mM indoxyl sulfate, 0.3 μM 5-aminolevulinic acid hydrochloride, 0.15 μM sodium ferrous citrate |

After culturing for 24 hours under the above culture conditions I to VI, the culture supernatant was separated, and the concentration of erythropoietin contained in the culture supernatant was measured with "Human Erythropoietin ELISA kit" (from Bender MedSystems).

The results of this Example are shown in FIG. 1. The unit for erythropoietin concentration in this figure is (mIU/ml).

In Group (III) with addition of TNF-α, decrease in the concentration of erythropoietin was observed compared to Group (I) without administration of the same. In addition, in Group (V) with addition of indoxyl sulfate, decrease in the concentration of erythropoietin was observed compared to Group (I) without administration of the same.

Moreover, Group (IV) with addition of aminolevulinic acid hydrochloride simultaneously with TNF-α showed significantly high erythropoietin concentration value compared to Group (III) with addition of TNF-α. In other words, it is seen that the reduction of erythropoietin production is significantly suppressed by administering ALA.

In addition, Group (VI) with addition of aminolevulinic acid hydrochloride simultaneously with indoxyl sulfate showed significantly high erythropoietin concentration value compared to Group (V) with addition of indoxyl sulfate. In other words, it is seen that the reduction of erythropoietin production is significantly suppressed by administering ALA.

The invention claimed is:

1. A method for promoting production of erythropoietin, comprising: administering to a subject with reduced erythropoietin production a therapeutically effective amount of a compound shown by the following Formula (I):

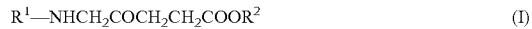

$$R^1-NHCH_2COCH_2CH_2COOR^2 \qquad (I)$$

wherein $R^1$ represents a hydrogen atom, and $R^2$ represents a hydrogen atom, or a salt thereof.

2. A method for treating anemia arising from reduction of erythropoietin production, comprising: administering to a subject with anemia arising from reduction of erythropoietin production an agent comprising a therapeutically effective amount of a compound shown by the following Formula (I):

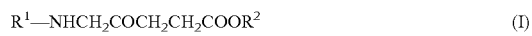

$$R^1-NHCH_2COCH_2CH_2COOR^2 \qquad (I)$$

wherein $R^1$ represents a hydrogen atom, and $R^2$ represents a hydrogen atom, or a salt thereof.

3. The method according to claim 2, characterized in that said agent further contains one or more metal-containing compounds.

4. The method according to claim 3, characterized in that said metal-containing compound is a compound containing a metal selected from the group consisting of iron, and zinc.

5. The method according to claim 3, characterized in that said metal compound is a compound containing iron.

6. The method according to claim 2 characterized in that said reduction of erythropoietin production is caused by inflammatory cytokine or uremic toxin.

7. The method according to claim 2, characterized in that said anemia is renal anemia.

8. The method according to claim 7, characterized in that said compound or a salt thereof promotes the production of erythropoietin.

9. The method according to claim 2, characterized in that said agent further contains one or more metal-containing compounds.

10. The method according to claim 2, characterized in that said anemia is renal anemia.

11. The method according to claim 3, characterized in that said anemia is renal anemia.

12. The method according to claim 4, characterized in that said anemia is renal anemia.

13. The method according to claim 5, characterized in that said anemia is renal anemia.

14. The method according to claim 6, characterized in that said anemia is renal anemia.

\* \* \* \* \*